United States Patent
DeCaro et al.

(10) Patent No.: US 10,428,306 B2
(45) Date of Patent: Oct. 1, 2019

(54) METHOD AND SYSTEM FOR TISSUE TREATMENT WITH CRITICAL/SUPERCRITICAL CARBON DIOXIDE

(71) Applicant: Warsaw Orthopedic, Inc., Warsaw, IN (US)

(72) Inventors: Mark DeCaro, Millstone Township, NJ (US); Guobao Wei, Milltown, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 252 days.

(21) Appl. No.: 15/235,202

(22) Filed: Aug. 12, 2016

(65) Prior Publication Data

US 2018/0044639 A1    Feb. 15, 2018

(51) Int. Cl.
| | | |
|---|---|---|
| A61F 2/28 | (2006.01) | |
| A61L 2/24 | (2006.01) | |
| A61L 27/46 | (2006.01) | |
| A61L 27/34 | (2006.01) | |
| A61K 35/32 | (2015.01) | |
| B01D 49/00 | (2006.01) | |
| C12N 5/077 | (2010.01) | |
| B01D 53/14 | (2006.01) | |
| B01D 11/02 | (2006.01) | |
| A61L 2/00 | (2006.01) | |

(52) U.S. Cl.
CPC .......... *C12N 5/0654* (2013.01); *A61L 2/0082* (2013.01); *A61L 2/24* (2013.01); *B01D 11/0203* (2013.01); *B01D 11/0207* (2013.01); *B01D 11/0284* (2013.01); *B01D 11/0292* (2013.01); *B01D 53/1487* (2013.01); *A61L 2202/14* (2013.01); *A61L 2202/20* (2013.01); *B01D 2252/103* (2013.01); *B01D 2256/22* (2013.01); *B01D 2258/02* (2013.01)

(58) Field of Classification Search
None
See application file for complete search history.

(56) References Cited

U.S. PATENT DOCUMENTS

| | | |
|---|---|---|
| 6,224,843 B1 | 5/2001 | Ahmed et al. |
| 7,055,333 B2 | 6/2006 | Leitch et al. |
| 8,007,718 B1 * | 8/2011 | Biberger ............... B22F 9/12 134/1 |
| 8,642,061 B2 | 2/2014 | Shimp et al. |
| 2002/0150522 A1 | 10/2002 | Heim et al. |
| 2003/0072677 A1 | 4/2003 | Kafesjian et al. |
| 2003/0161780 A1 | 8/2003 | Howard et al. |
| 2003/0221704 A1 | 12/2003 | Johnson et al. |
| 2005/0155379 A1 | 7/2005 | Gershtein et al. |
| 2009/0087471 A1 * | 4/2009 | Shimp ............... A61L 27/30 424/423 |
| 2009/0130173 A1 | 5/2009 | Behnam et al. |
| 2011/0070312 A1 | 3/2011 | Wei et al. |
| 2011/0265647 A1 | 11/2011 | Find et al. |
| 2013/0008182 A1 | 1/2013 | Hrudka |
| 2013/0079494 A1 | 3/2013 | Gleiman et al. |
| 2013/0111948 A1 | 5/2013 | Higginbotham |
| 2013/0269732 A1 | 10/2013 | Banerjee et al. |
| 2013/0282138 A1 | 10/2013 | McKay |
| 2014/0205674 A1 | 7/2014 | Wei |
| 2015/0202338 A1 | 7/2015 | Kibalo |
| 2015/0258245 A1 | 9/2015 | Behnam et al. |
| 2015/0306278 A1 | 10/2015 | McKay |
| 2016/0008409 A1 | 1/2016 | Joslyn et al. |

OTHER PUBLICATIONS

Gan Xu et al., "An Improved CO2 Separation and Purification System Based on Cryogenic Separation and Distillation Theory"; Energies Journal, 2014; pp. 3485-3502.

* cited by examiner

*Primary Examiner* — Soren Harward
*Assistant Examiner* — Paul D. Pyla

(57) ABSTRACT

Methods of decontaminating bone tissue and an apparatus or system for the same are provided. The methods can be multi-batch processes and include contacting the bone tissue having contaminants with carbon dioxide to decontaminate the bone tissue and to form carbon dioxide having contaminants. The contaminated carbon dioxide is collected and the contaminants are removed to obtain purified carbon dioxide which can be recycled to treat contaminated bone tissue. The contaminated carbon dioxide can be purified by bubbling it through water and/or an organic solvent followed by acid treatment, filtering and liquefying the carbon dioxide. Contaminants that can be removed from contaminated bone tissue, and in turn, from contaminated carbon dioxide include infectious organisms, bacteria, viruses, protozoa, parasites, fungi and mold or a mixture thereof.

13 Claims, 3 Drawing Sheets

METHOD AND SYSTEM FOR TISSUE TREATMENT WITH CRITICAL/SUPERCRITICAL CARBON DIOXIDE

BACKGROUND

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Autologous cancellous bone ("ACB"), also known as autograft or autogenous bone is considered the gold standard for bone grafts. ACB is osteoinductive and non-immunogenic, and, by definition, has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Much effort has been invested in the identification or development of alternative bone graft materials. In the procurement and processing of xenograft or allograft, a prime consideration is minimizing the risk of transferring potentially harmful diseases to the bone recipient. In fact, provision of bone tissue safe for transplantation provides a very special challenge as immunogenic material and also microorganisms and viruses can be found deep within the internal matrix of bone samples.

Transplanting of contaminated bone can have serious consequences to the recipient. For example, transmission of human immunodeficiency virus (HIV) via bone grafting is well known. Accordingly, there is a great need for bone processing methods that decrease the risk of disease transmission associated with the use of, and preparation and procurement of, transplantable bone to the recipient. In this regard it is also important to recognize that even with a state of the art donor screening methodology, recent infections in a particular donor may not be detected, thereby underscoring the importance of improved cleaning and decontaminating treatments that offer prophylactic protection against potential, or as yet undetected, infectious agents.

Current methods for viral inactivation and sterilization involve the use of toxic chemicals, high temperature and/or irradiation. The harsh treatment of biological active materials such as bone grafting materials cause the degradation or decomposition of materials, destroy biological activity, for example osteoconductivity of demineralized bone tissue, and reduce mechanical properties significantly.

There are also significant limitations on the extent to which decontaminating agents have been used successfully to penetrate and to decontaminate the bone matrix. Bone tissue contains potentially removable materials, for example, marrow, cells and lipids that impede access of decontaminating agents deep into bone tissue where infectious agents or immunogenic macromolecules may be present.

Methods have been developed for treating bone tissue with carbon dioxide as part of critical point dehydration. Other methods have used supercritical carbon dioxide to achieve viral inactivation and/or terminal sterilization of bone tissue. Some of these methods required large amounts of carbon dioxide which have been costly. The carbon dioxide used in the treatment of bone tissue would also become contaminated with infectious agents and/or other solvents and, when released to the atmosphere, would have a negative environmental impact. Because in some instances the treatment of bone tissue was not automated, human error would contribute to an inefficient process that would provide an inconsistent product.

Accordingly, there is a need for automated, efficient methods of treating bone tissue without compromising the integrity of desirable biomaterials present in bone tissue and at the same time reduce costs associated with the use of large amounts of carbon dioxide, reduce or even eliminate human error, and provide product consistency while improving the environment.

SUMMARY

Methods and systems are provided that allow automation in treating bone without comprising the integrity of desirable biomaterials present in bone tissue. Methods of decontaminating bone tissue using carbon dioxide and methods of purifying the contaminated carbon dioxide are provided. This is done to recycle the carbon dioxide so the contaminated carbon dioxide can be purified and re-used. The methods described in this application include contacting contaminated bone tissue with carbon dioxide to extract the contaminants from the bone tissue and form carbon dioxide having contaminants; collecting the carbon dioxide having contaminants and separating the contaminants from the collected carbon dioxide. In some embodiments, the purified carbon dioxide is recycled for use in treating the contaminated bone tissue. In other embodiments, the contaminated bone tissue can be treated in multiple batch processes wherein the purified carbon dioxide from one batch can be used to treat contaminated bone tissue in the next batch.

In some embodiments, the methods of purifying the contaminated carbon dioxide obtained from treatment of contaminated bone tissue with carbon dioxide include collecting the carbon dioxide having contaminants and separating the contaminants from the collected contaminated carbon dioxide to obtain the purified carbon dioxide. In some embodiments, the purified carbon dioxide is recycled for use in treating contaminated bone tissue.

An apparatus or system for treating contaminated bone tissue with purified carbon dioxide, purifying the contaminated carbon dioxide and recycling the purified carbon dioxide to treat contaminated bone tissue is also provided. In various embodiments, the system for treating contaminated bone tissue with purified carbon dioxide includes a bone tissue chamber configured for holding contaminated bone tissue and receiving purified carbon dioxide into the bone tissue chamber and evacuating contaminated carbon dioxide from the bone tissue chamber; a purified carbon dioxide supply configured for supplying purified carbon dioxide to the bone tissue chamber to decontaminate the bone tissue; a collection chamber configured to receive contaminated carbon dioxide from the bone tissue chamber and evacuate contaminated carbon dioxide from the collection chamber; and a purification chamber configured to receive contaminated carbon dioxide from the collection chamber and to remove contaminants from the contaminated carbon dioxide by a purification material to obtain purified carbon dioxide, the purification chamber configured to evacuate the purified carbon dioxide and supply it to the bone tissue chamber.

In some embodiments, the system for treating contaminated bone tissue with purified carbon dioxide also includes a controller and a signal transmission system functionally interconnecting the controller and the bone tissue chamber, the purified carbon dioxide supply, the collection chamber and the purification chamber. The controller can also include computer readable instructions to cause the controller to effect the evacuation of contaminated carbon dioxide from the bone tissue chamber to the collection chamber, send the contaminated carbon dioxide to the purification chamber, and dispense the purified carbon dioxide to the bone tissue chamber.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits and advantages of the embodiments will be apparent with regard to the following description, appended claims and accompanying drawing where:

DETAILED DESCRIPTION

Figure 1:
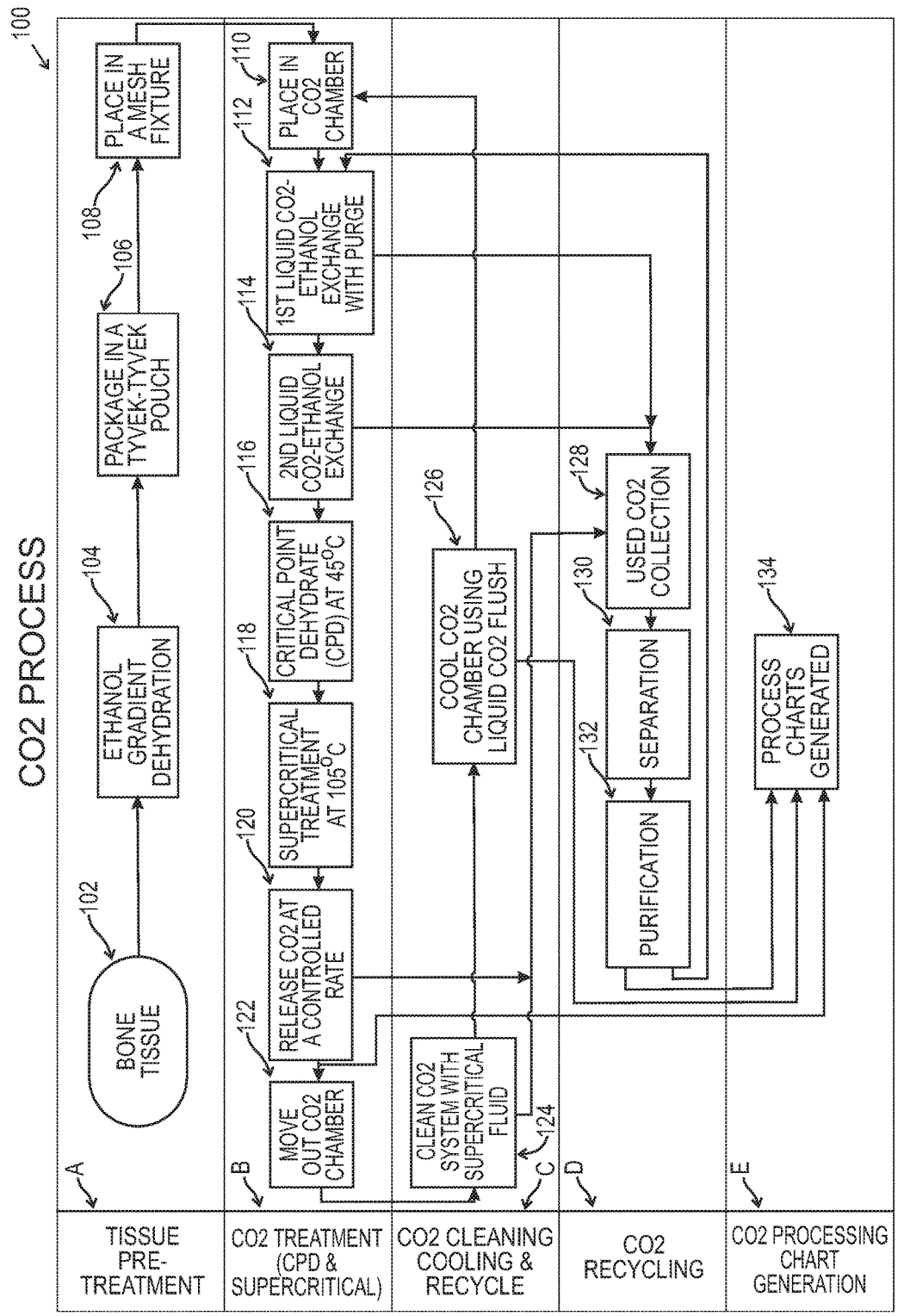
FIG. 1 illustrates a flow chart of a carbon dioxide method of treating bone tissue in accordance with one embodiment.

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated methods of decontaminating bone tissue, and such further applications of the principles of the disclosure as described herein being contemplated as would normally occur to one skilled in the art to which the disclosure relates.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin. Bone is also used in the most general sense and includes all types of human or animal bone tissue, including whole bones, bone pieces, bone blocks with attached connective tissues such as ligaments and tendons, as well as ground bone preparations and ground demineralized bone preparations.

Demineralized, as used herein, refers to any material generated by removing mineral material from tissue, for example, bone tissue. In certain embodiments, the demineralized compositions described herein include preparations containing less than 5% calcium. In some embodiments, the demineralized compositions may comprise less than 1% calcium by weight. Partially demineralized bone is intended to refer to preparations with greater than 5% calcium by weight but containing less than 100% of the original starting amount of calcium. In some embodiments, partially demineralized comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, demineralized bone has less than 95% of its original mineral content. In some embodiments, demineralized bone less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "demineralized" is intended to encompass such expressions as "substantially demineralized," "partially demineralized," "surface demineralized," and "fully demineralized." "Partially demineralized" is intended to encompass "surface demineralized."

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone activity refers to the osteoinductive activity of demineralized bone.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In other embodiments, the DBM compositions comprise partially demineralized bone (e.g., preparations with greater than 5% calcium by weight but containing less than 100% of the original starting amount of calcium) are also considered within the scope of this disclosure.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as a bone tumor. DBM is has been shown to promote bone formation in vivo by osteoconductive and osteoinductive processes. The osteoinductive effect of implanted DBM compositions results from the presence of active growth factors present on the isolated collagen-based matrix. These factors include members of the TGF-R, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

Lipid, as used herein, refers to any one or more of a group of fats or fat-like substances occurring in humans or animals. The fats or fat-like substances are characterized by their insolubility in water and solubility in organic solvents. Lipid also includes, but is not limited to, complex lipid, simple lipid, triglycerides, fatty acids, glycerophospholipids (phospholipids), true fats such as esters of fatty acids, glycerol, cerebrosides, waxes, and sterols such as cholesterol and ergosterol. As used herein, lipid also includes lipid-containing organisms, such as lipid-containing infectious agents. Lipid-containing infectious agents are defined as any infectious organism or infectious agent containing lipids. Such lipids may be found, for example, in a bacterial cell wall or viral envelope. Lipid-containing organisms include but are not limited to eukaryotic and prokaryotic organisms, bacteria, viruses, protozoa, mold, fungi, and other lipid-containing parasites.

Delipidation, as used herein, refers to the process of removing lipids from bone material or from a lipid-containing organisms contained in bone material or tissue.

Contaminants or infectious organisms, as used herein, refer to any lipid-containing infectious organism capable of causing infection. Some infectious organisms include bacteria, viruses, protozoa, parasites, fungi and mold.

Virus, as used herein, refers to viruses and virus-like particles including enveloped or lipid-coated viruses, and non-enveloped, protein encased viruses. A "virion" is an individual virus entity or particle. As used herein, the term "inactive" means the virion particle is unable to replicate or infect a host cell.

Osteoconductive, as used herein, refers to the ability of a substance to serve as a template or substance along which bone may grow.

Osteogenic, as used herein, refers to materials containing living cells capable of differentiation into bone tissue.

Osteoimplant, as used herein, refers to any implant prepared in accordance with the embodiments described herein and therefore may include expressions such as bone material, bone tissue, bone membrane, bone graft.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "partially demineralized" as used herein refers to bone-derived elements possessing from about 8 to about 90 weight percent of their original inorganic mineral content. In some embodiments, partially demineralized contains about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and/or 90 weight percent of their original inorganic mineral content. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In overall appearance the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are, in some embodiments, demineralized however some of the original mineral content may be retained when desirable for a particular embodiment.

Non-fibrous, as used herein, refers to elements that have an average width substantially larger than the average thickness of the fibrous bone element or aspect ratio of less than from about 50:1 to about 1000:1. In some aspects, the non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular".

Sterilization, as used herein, refers to an act or process using either physical or chemical means for eliminating or inactivating substantially all viable organisms, especially micro-organisms, viruses and other pathogens, associated with a xenograft or bioprosthetic device. As used herein, "sterilized" includes bone material or bone tissue achieving a sterility assurance level of $10^{-6}$ colony forming unit (CFU), as determined by FDA (Federal Drug Administration) standards.

Supercritical fluid, as used herein, refers to a substance at a temperature and pressure above its thermodynamic critical point. Under these conditions, the distinction between gases and liquids does not apply and the substance is described as a fluid. Under these conditions, a supercritical fluid has the ability to diffuse through solids like a gas, and dissolve materials like a liquid. Additionally, a supercritical fluid can readily change in density upon minor changes in temperature or pressure.

Supercritical carbon dioxide, as used herein, refers to carbon dioxide ($CO_2$) above its thermodynamic critical point (i.e., above critical temperature of 31.1° C. and pressure of 1100 psi). Supercritical carbon dioxide is an excellent nonpolar solvent for many organic compounds. It has been likened to a solvent resembling hexane, though with some hydrogen-bonding acceptor capability and some dipole selectivity. Alkenes, alkanes, aromatics, ketones, and alcohols (up to a relative molecular mass of around 400) dissolve in supercritical carbon dioxide. Very polar molecules such as sugars or amino acids and most inorganic salts are insoluble. By adjusting the pressure of the fluid, the solvent properties can be adjusted to more "gas-like" or more "liquid-like", which allows tuning of the solvent properties.

Introduction

The present application is directed to the automated use of critical and/or supercritical carbon dioxide in preparing decontaminated bone tissue for incorporation into xenografts and bioprosthetic devices. Supercritical fluids such as carbon dioxide can be used to remove lipids, contaminants or inactivate infectious agents from the bone tissue under conditions which do not significantly degrade or denature tissue proteins. The process and apparatus of this application also includes the automated purification of the carbon dioxide that has become contaminated in the process of decontaminating the bone tissue. The contaminated carbon dioxide is collected, purified, liquefied and recycled for further use in decontaminating the bone tissue contaminated with disease causing pathogens, viruses, bacteria, fungi, mildew or a mixture thereof. The methods and apparatus for treatment of contaminated bone tissue described in this disclosure can be a multi batch design. Such an approach is more economical because it allows for the recycling of purified carbon dioxide rather than the continuous feeding of carbon dioxide from an outside source. Recycling carbon dioxide also avoids releasing contaminated carbon dioxide reducing not only the overall process costs but also improving the environment.

Carbon Dioxide Processing and Apparatus

FIG. 1 illustrates a flow diagram of a carbon dioxide process 100 for decontamination of bone tissue 102 contaminated with infectious organisms such as bacteria, viruses, protozoa, parasites, fungi and mold. Further, in some aspects, the contaminated bone tissue also includes lipids, cells and marrow which could interfere with bone decontamination and are undesirable in a bone tissue for use to repair bone defects and as bone grafting material. However, it is desirable to preserve beneficial biomaterial in the bone tissue, such as for example, collagen, osteogenic factors, etc. that allow bone growth and integration of the implant when the bone tissue is implanted into a bone defect or cavity.

In various embodiments, contaminated bone tissue can have these undesirable contaminants removed with liquefied, critical or supercritical carbon dioxide, which extract the contaminants from the bone tissue, and in turn, become contaminated or spent. Contaminated or spent carbon dioxide can then be purified and recycled back for bone tissue decontamination using the carbon dioxide process 100.

Carbon dioxide process 100, in various aspects, includes 5 processing stages. In stage A, the contaminated bone tissue of step 102 is pre-treated by ethanol gradient dehydration in step 104, then packaged in a Tyvek pouch in step 106 or placed in a mesh covering or delivery fixture in step 108 for further processing in stage B. In stage B, the contaminated bone tissue of step 110 is treated with liquid carbon dioxide (steps 112 and 114) and/or further subjected to critical point dehydration (CPD) at 45° C. in step 116 and/or treatment with supercritical carbon dioxide at 105° C. in step 118. The carbon dioxide containing contaminants extracted from the treatment of the contaminated bone tissue can be released at a controlled rate in step 120 for further processing in stage D, the carbon dioxide recycling stage. In stage B, the contaminated or spent carbon dioxide can be removed (step 122) from the carbon dioxide chamber and moved to stages C and D of carbon dioxide processing system 100, for further cleaning and/or purifying. In stage C, the contaminated carbon dioxide is cleaned with supercritical fluid in step 124, and sent to recycling stage D for further processing. Some of the cleaned carbon dioxide from step 124 can be and used to cool the carbon dioxide chamber of step 110 by flushing it with liquid carbon dioxide in step 126. In stage D, the carbon dioxide recycling stage, the contaminated carbon dioxide is collected in step 128, separated from its contaminants in step 130 and purified in step 132. In the final stage E, the level of purity of the purified carbon dioxide and other processing parameters from stages B and C can be measured by generating processing charts 134.

In some embodiments, the bone tissue of step 102 may be pre-treated to remove water prior to the critical point drying of stage B. Thus, after demineralization, in some aspects, bone tissue samples (in water) may be dehydrated to remove residual water content. Such dehydration may be accomplished, for example, through a series of graded ethanol solutions (for example, 20%, 50%, 70%, 80%, 90%, 95%, 100% ethanol in deionized water) as illustrated in step 104 of FIG. 1. In other embodiments, penetrating the bone tissue with a graded series of ethanol solutions or alcohols may be accomplished in an automated fashion. For example, pressure and vacuum could be used to accelerate penetration into the bone tissue.

In alternative embodiments, other means or procedures for removing water (drying or dehydrating) from the bone tissue may be used. For example, the bone tissue may be washed with other dehydrating liquids such as acetone to remove water, exploiting the complete miscibility of these two fluids. The acetone may then be washed away with high pressure liquid carbon dioxide.

The dehydrated but still contaminated bone tissue can be packaged in a delivery vehicle such as a carrier or covering, for example in a Tyvek pouch as in step 106 or a polymer mesh as in step 108, both illustrated in FIG. 1. For example, a polymer mesh covering is useful because under controlled pressure, temperature, treating time, and carbon dioxide release, the polymer structures are not affected.

The dehydrated bone tissue is further placed into a carbon dioxide chamber or container used in step 110 for further treatment with carbon dioxide. In the carbon dioxide chamber, the dehydrated bone tissue is flushed with a first liquefied carbon dioxide stream in step 112 to extract any ethanol retained from the ethanol gradient dehydration step 104. Flushing with liquid carbon dioxide may be done one or more times. For example, in the process illustrated in FIG. 1, flushing with liquid carbon dioxide is performed a second time at step 114.

In some embodiments, the bone tissue is further subjected to critical point drying which is carried out using carbon dioxide as illustrated at step 116. The critical point for carbon dioxide is 304.25 K at 7.39 MPa or 31.1° C. at 1072 psi or 31.2° C. and 73.8 bar. To perform critical point drying, the temperature and pressure may continue to be raised, for example to 40° C. with corresponding pressure of 85 bar. In the embodiment illustrated in FIG. 1, the temperature in step 116 at which critical point dehydration occurs is raised to 45° C. Thus, in some embodiments, the liquid carbon dioxide is heated until its pressure is at or above the critical point, at which time the pressure can be gradually released, allowing the gas to escape and leaving a dried product.

In certain embodiments, bone fibers processed using CPD have a BET surface area from about 1 to about 5 $m^2$/gm, a value 3 or 4 times greater than lyophilized bone fibers. In other embodiments, DBM fibers processed using CPD have a BET area surface from about 40 to about 100 $m^2$/gm, a value 100 times greater than when DBM fibers are lyophilized.

In a further embodiment, the critical point dried bone tissue may further be treated, or alternatively be treated, with supercritical carbon dioxide (carbon dioxide above the critical point) as shown at step 118 of FIG. 1. Supercritical carbon dioxide may also be useful in viral inactivation. In some embodiments, thus, the bone tissue is placed in a supercritical carbon dioxide chamber and liquid carbon dioxide is introduced, for example, by an air pump. The temperature is raised to 105° C. with corresponding pressure about 485 bar. In alternative embodiments, other temperatures and/or pressures above the critical point of carbon dioxide may be used. The samples are soaked in supercritical carbon dioxide for a certain time and carbon dioxide is released. The resulting bone samples retain surface morphologies, hence surface area, and osteoinductivity after such treatment.

In yet a further embodiment, monolithic bone is demineralized and particulated before drying. Accordingly, the bone may be demineralized in monolithic pieces. The demineralized monolithic pieces may then be milled in a wet condition and critical point dried, for example using carbon dioxide as a medium.

With further reference to FIG. 1, in various embodiments, the carbon dioxide carrying the contaminants extracted from the contaminated bone tissue is collected in a used or spent carbon dioxide collection step 128. Spent or contaminated carbon dioxide of step 128 is collected into a collection chamber or container configured to receive contaminated carbon dioxide from bone tissue treatment step 110 via the $1^{st}$ and $2^{nd}$ liquefied carbon dioxide ethanol exchanges steps 112 and 114. The collection chamber used in step 128 can also evacuate the contaminated or spent carbon dioxide to a separation step 130 and/or a purification step 132.

The separation step 130 can be performed in a separation chamber using several separation steps. In one embodiment, the contaminated or spent carbon dioxide is bubbled through water and/or an organic solvent to remove additional amounts of alcohol that may not have been removed in previous processing steps. In other embodiments, the carbon dioxide bubbled through water and/or organic solvent is further subjected to acid treatment, filtering and liquefaction so that other contaminants such as lipids, proteins bacteria and viruses can be removed. Further purification occurs at step 132, wherein the carbon dioxide is passed through filters having different pore sizes. Depending on the type of contaminants still present in the liquefied carbon dioxide stream, useful purification filters can have pores varying from about 0.2 μm, 1, 2, 3, 4, 5, 6, 7, 8, 9, 10, 20, 30, 40, 50, 60, 70, 80, 90 to about 100 μm. In various embodiments, the purified carbon dioxide is up to 95.0%, 96.0, 97.0, 98.0, 99.1, 99.2, 99.3, 99.4, 99.5, 99.6, 99.7, 99.8 to 99.9% free of lipids, disease carrying pathogens, viruses, bacteria, fungi, mildew or mixtures thereof.

Figure 2A:
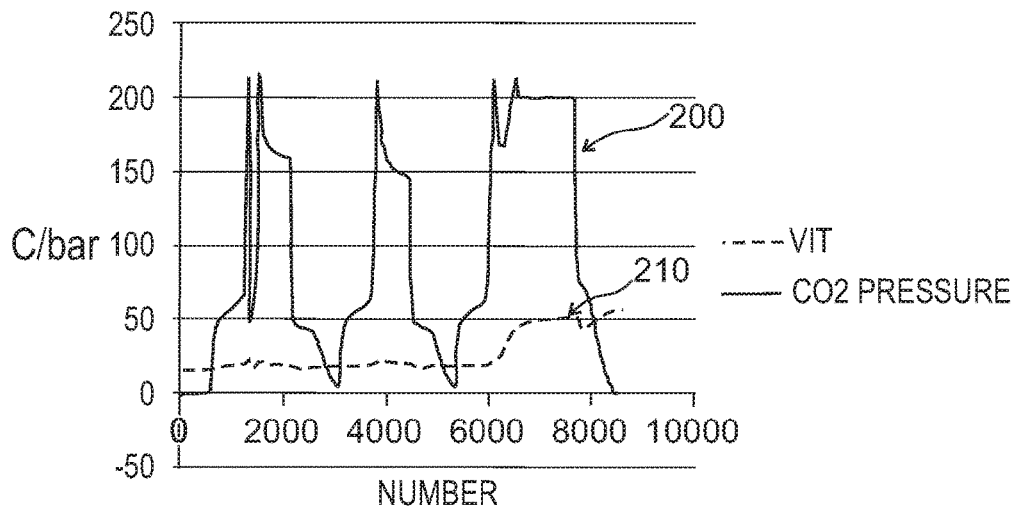
FIG. 2A illustrates a process chart showing the vanishing interface tension and carbon dioxide pressure for a fiber bone tissue treated in accordance with one embodiment.
Figure 2B:
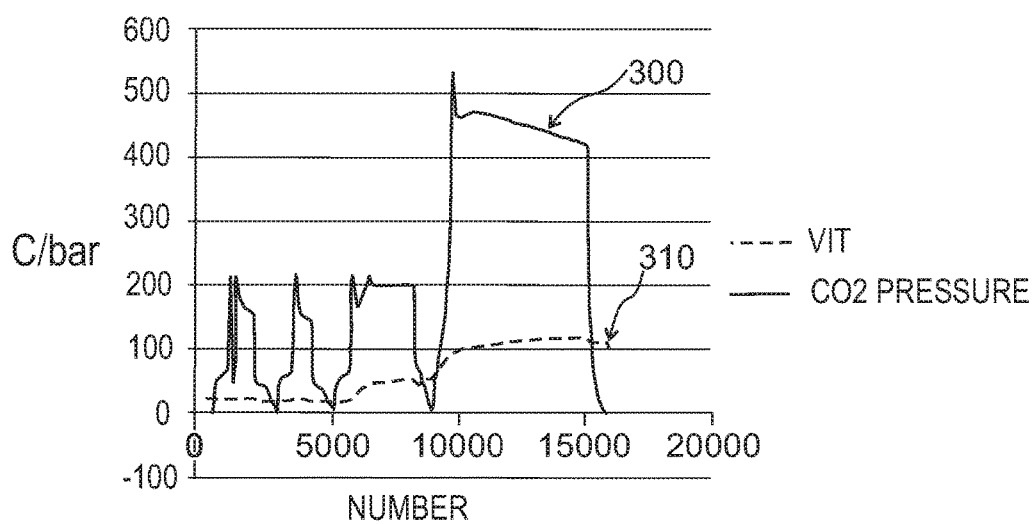
FIG. 2B illustrates a process chart showing the vanishing interface tension and carbon dioxide pressure for a chip bone tissue treated in accordance with another embodiment.

The purified liquid carbon dioxide is subsequently recycled to stage B carbon dioxide treatment of the contaminated bone tissue, in some aspects, to steps 112 and 114 ethanol extraction steps. The level of purification achieved together with other properties of steps 126 and 120 can be ascertained from process charts 134 generated in stage E of the carbon dioxide processing system 100. In various embodiments, process charts are generated as illustrated in FIGS. 2A and 2B. The process chart illustrated in FIG. 2A measures the vanishing interface tension (VIT) 210 and carbon dioxide pressure 200 for a treated fiber bone tissue. FIG. 2B depicts VIT measurements 310 and carbon dioxide pressure 300 for a treated chip bone tissue.

Figure 3:
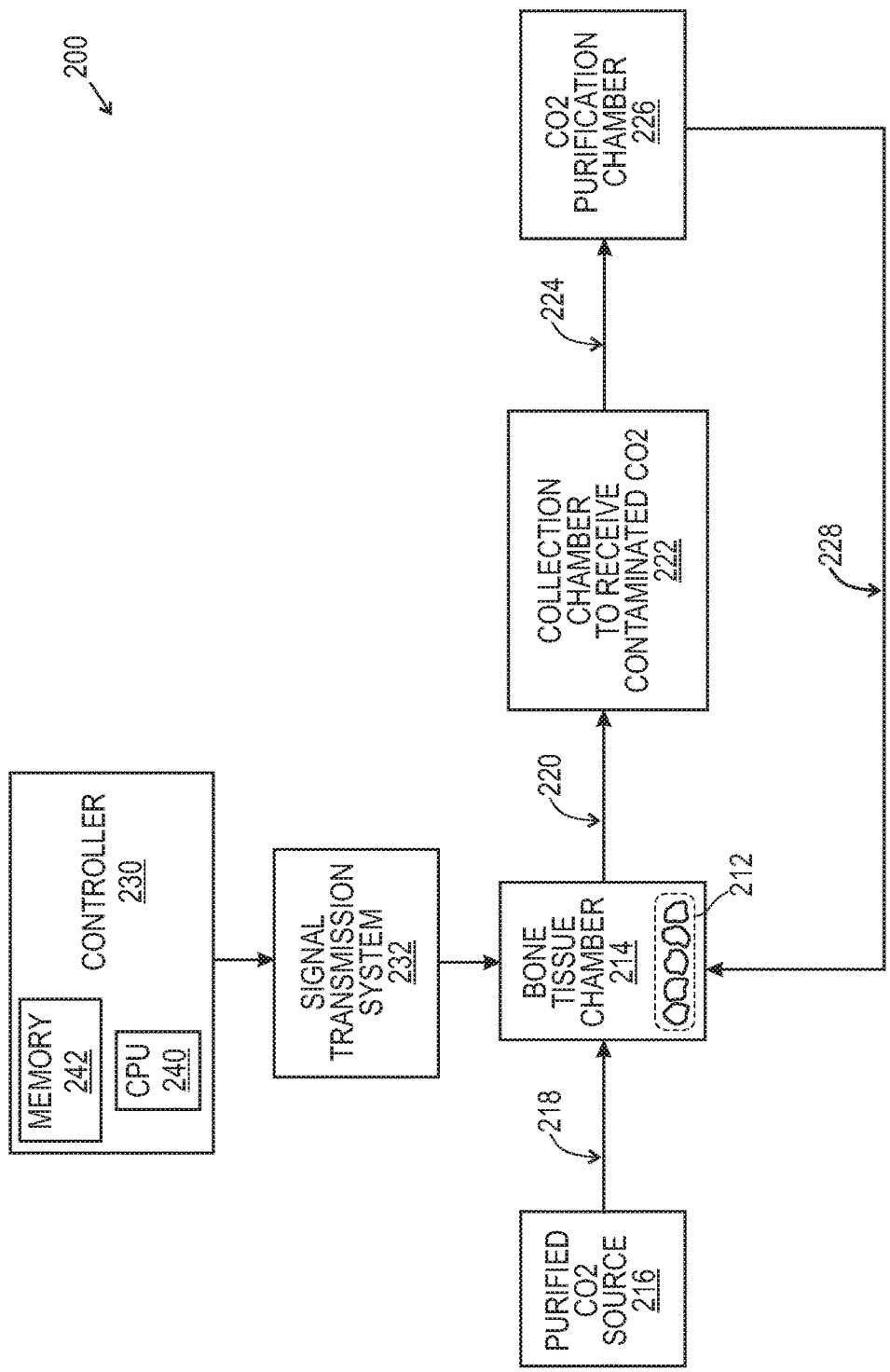
FIG. 3 is a simplified schematic of an embodiment of an apparatus or system for treating contaminated bone tissue; and It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

FIG. 3 is a simplified schematic of an embodiment of an apparatus or system 200 for treating contaminated bone tissue 212. System 200 includes a bone tissue chamber 214 configured for holding bone tissue contaminated with typical bone tissue contaminants, for example disease carrying pathogens, bacteria protozoa, viruses, fungi, mildew or a mixture thereof. In some embodiments, lipids entrapped in bone tissue can also be removed with supercritical carbon dioxide. The bone tissue chamber 214, configured for holding contaminated bone tissue 212, is also configured for receiving purified carbon dioxide from a purified carbon dioxide source 216 through conduit 218 and for evacuating carbon dioxide contaminated with the contaminants present in the contaminated bone tissue through conduit 220 to a collection chamber 222. In some embodiments, the purified carbon dioxide supply 216 can be an external source, such as bottled carbon dioxide pressurized containers and/or a purified carbon dioxide reservoir.

The contaminated carbon dioxide from the bone tissue chamber 214 flows through conduit 220 to the collection chamber 222 from which the contaminated carbon dioxide is evacuated through conduit 224 to a carbon dioxide purification chamber or system 226. In the purification chamber or system 226, the contaminated carbon dioxide is purified to remove contaminants to about 99.9% free of lipids, disease causing pathogens, viruses, bacteria, fungi, mildew or a mixture thereof. The carbon dioxide purification chamber or system 226 is configured to receive contaminated carbon dioxide from the collection chamber 222 and to evacuate the purified carbon dioxide through conduit 228 in order to recycle the purified carbon dioxide, where the process can re-start and the recycled carbon dioxide can be re-used and introduced into the bone tissue chamber 214. If additional carbon dioxide is needed, it can be introduced from a purified carbon dioxide source 216 through conduit 218 and into the bone tissue chamber 214.

The apparatus or system 200 for treating contaminated bone tissue with recycled purified carbon dioxide can significantly reduce the cost and complexity of a supply of purified carbon dioxide only form an external source. By recycling the purified carbon dioxide to the bone tissue chamber, the amount and cost of externally delivered carbon dioxide is substantially reduced. In addition, the automation of the purification of the carbon dioxide purification treatment for bone fibers and/or bone chips is reduced to a few steps, significantly reducing human error and improving the reliability of the carbon dioxide treatment process by eliminating potential carbon dioxide non-conformance steps.

In some embodiments, the system for treating contaminated bone tissue with carbon dioxide further comprises a controller 230 and a signal transmission system 232 functionally interconnecting the controller 230 with all other elements of the system 200 for treatment of contaminated bone tissue 212, namely, the bone tissue chamber 214, the purified carbon dioxide source 216, the contaminated carbon dioxide collection chamber 222, the purification chamber of contaminated carbon dioxide 226 as well as their interconnecting conduits. For purposes of this disclosure, the controller 230 may be embodied as a general purpose computer, for example a personal computer, or as an industrial type controller. The controller 230 can include a CPU 240, a memory 242, an input/output (I/O) unit, an input unit, a display device, a printing device not shown in FIG. 3. The display device, input device and printing device, need not be integral with the controller 230, but may be functionally connected to the CPU 240 and/or external to a housing enclosing the CPU 240. The display device may be embodied as any type of device capable of visually communicating with an operator of the apparatus or system 200 for treating contaminated bone tissue, such as, without limitation, one or more annunciators, digital displays, flat panel displays, CRTs, or other devices capable of providing visual indications relating functioning of the system 200. The input device may be embodied as buttons, knobs, keypads, touch pads, a computer mouse or trackball, a keyboard, a microphone and voice recognition software and associated hardware, or other input device, either integral with the housing of the controller 230 or external to the housing of the controller. The printing device may be embodied as any device capable of providing a hard copy output. A sound transducer optionally is provided to effect audible communication relating operation of the controller 230. The memory 242 comprises any combination of RAM, ROM, hard drive, flash drive, or CD reader and disc, as required to store instructions to operate the CPU 240 to effect control of the system 200. The memory 242 has stored therein instructions in the form of executable programming. Those skilled in the art will appreciate that software executing procedures describe herein may be written in any language which can be compiled to operate the CPU 240. It will be understood that controller 230 can be linked to a plurality of sensors that detect the level of carbon dioxide in each of the chambers to detect low, desired, and high levels of carbon dioxide as well as temperature, pressure in the chambers and the supply of carbon dioxide to those chambers in the outlets and inlets can be regulated by the controller 230.

Providing Delipidation

In various embodiments, the carbon dioxide process 100 of FIG. 1 can be utilized for delipidation of fats present in the bone tissue. Easily available and cheap, carbon dioxide is non-toxic, non-corrosive and non-flammable and, thus well suited for delipidation of bone tissue. Moreover, because carbon dioxide has low viscosity and high diffusion coefficients, supercritical carbon dioxide can be used to reach components entrapped in bone tissue, such as lipids. The result is that carbon dioxide in the supercritical state dissolves the essentially lipidic organic matter present in the bone tissue easily and virtually completely. The risks to the immune system and of infection from contaminated bone tissue are thereby considerably reduced.

In various embodiments, methods are provided for removing at least a lipid from bone tissue, the method comprising contacting the bone tissue with an effective amount of supercritical carbon dioxide thereby obtaining a substantially delipidated bone tissue. In some embodiments, bone tissue subjected to the delipidation methods described herein can be 99%, 99.5% or 99.9% free of lipids. The treated bone tissue itself will contain less than 1%, 0.5% or 0.1% fat on average after treatment, and this amount is evenly distributed.

Terminal Sterilization Using Supercritical Carbon Dioxide

In various aspects, the present application provides methods of removing from bone tissue contaminants such as bacteria, viruses, fungi, protozoa and mixtures thereof. The method comprises contacting the bone tissue with an effective amount of supercritical carbon dioxide sufficient to remove 99.0%, 99.5% or 99.9% of contaminants.

Some bacteria which may be treated by sterilization with supercritical carbon dioxide include, but are not limited to the following: *Staphylococcus; Streptococcus*, including *S. pyogenes; Enterococci; Bacillus*, including *Bacillus anthracis*, and *Lactobacillus; Listeria; Corynebacterium diphtherias; Gardnerella* including *G. vaginalis; Nocardia; Streptomyces; Thermoactinomyces vulgaris; Treponema; Camplyobacter; Pseudomonas* including *P. aeruginosa; Legionella; Neisseria* including *N. gonorrhoeae* and *N. meningitides; Flavobacterium* including *F. meningosepticum* and *F. odoratum; Brucella; Bordetella* including *B. pertussis* and *B. bronchiseptica; Escherichia* including *E. coli; Klebsiella; Enterobacter; Serratia* including *S. marcescens* and *S. liquefaciens; Edwardsiella; Proteus* including *P. mirabilis* and *P. vulgaris; Streptobacillus; Rickettsiaceae* including *R. rickettsii; Chlamydia* including *C. psittaci* and *C. trachomatis; Mycobacterium* including *M. tuberculosis, M. intracellulare, M. fortuitum, M. laprae, M. avium, M. bovis, M. africanum, M. kansasii, M. intracellulare*, and *M. lepraemurium*; and *Nocardia*, and any other bacteria containing lipid in their membranes.

Exemplary infectious agents removed from the tissue using the process of the application include, viruses, bacteria, mycobacteria, mycoplasma, fungi, prions and constituents thereof. Methods of this application are applicable to removing viruses of the family of Togaviridae, in particular of the genus Alphavirus, such as the Hepatitis C virus, and for preventing their transmission during tissue grafts; for combating viruses of the family Picorviridae, in particular of the genus Enterovirus, more particularly the Polio Sabin virus, and preventing their transmission during tissue grafts; for combating viruses of the family Herpesviridae and preventing their transmission during tissue grafts; for combating viruses of the family Retroviridae, in particular of the genus Lentivirus, more particularly human HIV immunodeficiency viruses, and preventing their transmission during tissue grafts. Of particular interest is the use of the methods of the present application to remove prions from contaminated bone tissue.

Embodiments of this application provide methods for inactivating viruses, especially enveloped or lipid-coated viruses, and nonenveloped, protein encased viruses in proteinaceous products without incurring substantial denaturation.

Supercritical carbon dioxide is useful in methods and apparatus for inactivating virus and virus-like particles present in contaminated bone tissues. One embodiment of the present application is directed to a method of inactivating one or more virions associated with a contaminated bone tissue. In one aspect, the method comprises the steps of contacting a bone tissue with a critical, near critical or supercritical carbon dioxide. The critical, near critical or supercritical carbon dioxide is capable of being received by at least one virion and upon removal, causes inactivation of the virion. The method further comprises the step of removing the critical, supercritical or near critical carbon dioxide from the material and one or more virions to render one or more virions inactive.

Viral infectious organisms which may be inactivated by the methods described herein include, but are not limited to the lipid-containing viruses of the following genuses: Alphavirus (alphaviruses), Rubivurus (rubella virus), Flavivirus (Flaviviruses), Pestivirus (mucosal disease viruses), (unnamed, hepatitis C virus), Coronavirus, (Coronaviruses), Torovirus, (toroviruses), Arteivirus, (arteriviruses), Paramyxovirus, (Paramyxoviruses), Rubulavirus (rubulaviruses), Morbillivirus (morbilliviruses), Pneumovirinae (the pneumoviruses), Pneumovirus (pneumoviruses), Vesiculovirus (vesiculoviruses), Lyssavirus (lyssaviruses), Ephemerovirus (ephemeroviruses), Cytorhabdovirus (plant rhabdovirus group A), Nucleorhabdovirus (plant rhabdovirus group B), Filovirus (filoviruses), Influenzavirus A, B (influenza A and B viruses), Influenza virus C (influenza C virus), (unnamed, Thogoto-like viruses), Bunyavirus (bunyaviruses), Phlebovirus (phleboviruses), Nairovirus (nairoviruses), Hantavirus (hantaviruses), Tospovirus (tospoviruses), Arenavirus (arenaviruses), unnamed mammalian type B retroviruses, unnamed, mammalian and reptilian type C retroviruses, unnamed type D retroviruses, Lentivirus (lentiviruses), Spumavirus (spumaviruses), Orthohepadnavirus (hepadnaviruses of mammals), Avihepadnavirus (hepadnaviruses of birds), Simplexvirus (simplexviruses), Varicellovirus (varicelloviruses), Betaherpesvirinae (the cytomegaloviruses), Cytomegalovirus (cytomegaloviruses), Muromegalovirus (murine cytomegaloviruses), Roseolovirus (human herpes virus 6), Gammaherpesvirinae (the lymphocyte-associated herpes viruses), Lymphocryptovirus (Epstein-Bar-like viruses), Rhadinovirus (saimiri-ateles-like herpes viruses), Orthopoxvirus (orthopoxviruses), Parapoxvirus (parapoxviruses), Avipoxvirus (fowl pox viruses), Capripoxvirus (sheeppoxlike viruses), Leporipoxvirus (myxomaviruses), Suipoxvirus (swine-pox viruses), Molluscipoxvirus (molluscum contagiosum viruses), Yatapoxvirus (yabapox and tanapox viruses), Unnamed, African swine fever-like viruses, Iridovirus (small iridescent insect viruses), Ranavirus (front iridoviruses), Lymphocystivirus (lymphocystis viruses of fish), Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxyiridae, and any other lipid-containing virus.

These viruses include the following human and animal pathogens: Ross River virus, fever virus, dengue viruses, Murray Valley encephalitis virus, tick-borne encephalitis viruses (including European and far eastern tick-borne encephalitis viruses), human coronaviruses 229-E and OC43 and others (causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, Arenaviruss: lymphocytic choriomeningitis (LCM) virus; Lassa virus, human immunodeficiency viruses 1 and 2, or any other immunodeficiency virus, hepatitis A virus, hepatitis B virus, hepatitis C virus, Subfamily: human herpes viruses 1 and 2, herpes virus B, Epstein-Barr virus), (smallpox) virus, cowpox virus, molluscum contagiosum virus.

All protozoa containing lipid, especially in their plasma membranes, are included within the scope of the present application. Protozoa that may be inactivated by treatment of the contaminated bone tissue with carbon dioxide at critical and supercritical conditions include, but are not limited to, the following lipid-containing protozoa: *Trypanosoma brucei, Trypanosoma gambiense, Trypanosoma cruzi, Leishmania donovani, Leishmania vianni, Leishmania tropica, Giardia lamblia, Giardia intestinalis; Trichomonas vaginalis, Entamoeba histolytica, Entamoeba coli, Entamoeba hartmanni, Naegleria* species, *Acanthamoeba* species, *Plasmodium falciparum, Plasmodium vivax, Plasmodium malariae, Plasmodium ovale, Toxoplasma gondii, Cryptosporidium parvum, Cryptosporidium muris, Isospora belli, Cyclospora cayetansis, Balantidium* species, *Babesia bovis, Babesia, microti, Babesia divergens, Encephalitozoon intestinalis, Pleistophora* species, *Nosema ocularum, Vittaforma corneae, Septata intestinalis, Enterocytozoon, Dientamoeba fragilis, Blastocystis* species, *Sarcocystis* species, *Pneumocystis carinii, Microsporidium africanum, Microsporidium ceylonensis, Eimeria acervulina, Eimeria maxima, Eimeria tenella* and *Neospora caninum*. It is to be understood that the present application is not limited to the protozoa provided in the list above.

In some embodiments, protozoa treated with methods of the present application is Coccidia, which includes *Isospora* species, *Cryptosporidium* species, *Cyclospora* species, *Toxoplasma* species, *Sarcocystis* species, *Neospora* species, and *Eimeria* species. These coccidian parasites cause intestinal disease, lymphadenopathy, encephalitis, myocarditis, and pneumonitis.

The terms "protozoal infection" or "infectious disease" mean diseases caused by protozoal infectious organisms. The diseases include, but are not limited to, African sleeping sickness, Chagas' disease, Leishmaniasis, Giardiasis, Trichomoniasis, amebiasis, primary amebic encephalitis, granulomatous amebic encephalitis, malaria, Toxoplasmosis, Cryptosporidiosis, Isosporiasis, Cyclosporiasis, Balantidiasis, Babesiosis, microsporidiosis, *Dientamoeba fragilis* infection, *Blastocystis hominis* infection, Sarcosporidiosis, pneumonia, and coccidiosis. A protozoal infection treated with the method of the present application is Coccidiosis, which is caused by *Isospora* species, *Cryptosporidium* species, *Cyclospora* species, *Toxoplasma* species, *Sarcocystis* species, *Neospora* species, and *Eimeria* species. These coccidian parasites cause human intestinal disease, lymphadenopathy, encephalitis, myocarditis, and pneumonitis. These coccidian parasites also cause disease in animals, including cattle, dogs, cats, and birds. Avians, and chickens, turkeys and quail in particular, are affected by Coccidiosis, especially by *Eimeria* species such as *E. acervulina, E. maxima, E. necatrix, E. bruneti, E. mitis, E. praecox* and *E. tenella*.

Providing Bone Tissue

The methods of delipidation and decontamination provided by this application apply broadly to bone tissue obtained from any source. In various embodiments, in xenogenic implantation in a human subject, bone can be obtained from animal sources such as cows and pigs. In other embodiments, in allogenic implantation in a human subject, bone is obtained from human cadavers, following appropriate ethical and legal requirements. Such human bone tissue is available from a variety of tissue banks.

The bone may comprise cortical bone, cancellous bone, or a combination thereof. Cancellous bone is available in a range of porosities based on the location in the body from which the bone is harvested. Highly porous cancellous bone may be harvested from various areas such as the iliac crest, while less porous bone may be harvested from areas such as the tibial condyle femoral head, and calcaneus. Cortical bone may be obtained from long bones, such as the diaphyseal shaft of the femur and tibia. In certain embodiments, the bone implant comprises cortical bone.

Depending on the desired end-use of the bone composition, the bone tissue may be subjected to mechanical processing. Such processing may include cutting and shaping, in embodiments forming a construct such as a bone pin or disk for implanting. In one embodiment, the present application provides a bone powder. In such an embodiment, the bone is initially ground to a selected size. In one embodiment, the bone particulates are less than about 1500 microns in size. In various embodiments, the bone particles range from about 50 microns to about 1000 microns, from about 75 to about 800 microns, or from about 150 to about 600 microns. Depending on the desired composition, particles may be of a variety of sizes.

In some embodiments, biological activities of the bone tissue may be increased. Accordingly, the bone tissue, and compositions formed from the bone tissue, may variously be referred to as biologically active and/or, in some cases, osteoinductive. The biological activities of the bone composition provided herein that may be increased include, but are not limited to, osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, exocytosis or endocytosis-inducing activity, or other cell or biological activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

Providing Bone Particles

The bone-derived tissue may be derived from any vertebrate. In certain embodiments, that the source of the bone tissue can be matched to the eventual recipient of the inventive composition (i.e., the donor and recipient should, at least, be of the same species). For example, human bone-derived tissue is typically used in a human subject. In other embodiments, the bone particles are obtained from bone of xenogenic origin. Porcine bone and bovine bone are particularly advantageous types of xenogenic bone tissue that can be used individually or in combination as sources for the bone particles. Xenogenic bone tissue may be combined with allogenic or autogenous bone.

Methods for the preparation of bone particles are known in the art. Bone particles can be formed by milling whole bone to produce fibers, chipping whole bone, cutting whole bone, fracturing whole bone in liquid nitrogen, or otherwise disintegrating the bone tissue. In certain embodiments, particles are sieved to produce particles of a specific size range. Bone particles may be of any shape or size. Exemplary shapes include spheroidal, plates, fibers, cuboidal, sheets, rods, oval, strings, elongated particles, wedges, discs, rectangular, polyhedral. In some embodiments, bone particles may be between about 10 microns and about 1000 microns in diameter or more. In some embodiments, particles may be between about 20 microns and about 800 microns in diameter or more. In certain embodiments, the particles range in size from approximately 100 microns in diameter to approximately 500 microns in diameter. In certain embodiments, the particles range in size from approximately 300 microns in diameter to approximately 800 microns in diameter. As for irregularly shaped particles, the recited dimension ranges may represent the length of the greatest or smallest dimension of the particle.

In certain embodiments, the bone-derived particles are used "as is" in preparing the inventive composites. In other embodiments, the bone-derived particles are modified before composite preparation. Thus, for example, bone particles suitable for use in the methods of the present application can be demineralized, non-demineralized, mineralized/deorganified, or anorganic bone particles.

Providing Demineralized Bone Tissue

Following shaving, milling or other technique whereby they are obtained, the bone tissue is subjected to demineralization in order to reduce its inorganic content to a very low level, in some embodiments, to not more than about 5% by weight of residual calcium and, in other aspects, to not more than about 1% by weight residual calcium.

Demineralization of the bone tissue ordinarily results in its contraction to some extent. Bone used in the methods described herein may be autograft, allograft, or xenograft. In various embodiments, the bone may be cortical bone, cancellous bone, or cortico-cancellous bone. While specific discussion is made herein to demineralized bone tissue, bone tissue treated in accordance with the teachings herein may be non-demineralized, demineralized, partially demineralized, or surface demineralized. The following discussion applies to demineralized, partially demineralized, and surface demineralized bone tissue. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone tissue can be conducted in accordance with known conventional procedures. For example, in a demineralization procedure, the bone tissue useful for the methods of this disclosure is subjected to an acid demineralization step that is followed by a defatting/disinfecting step. The bone tissue is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. The defatting/disinfecting step can be accomplished by the method of delipidation/terminal sterilization utilizing contacting the bone tissue with supercritical fluid as described in this application. Thus, in various embodiments, the bone tissue may be fully demineralized, partially demineralized, or surface demineralized.

In other embodiments, the delipidation/terminal sterilization methods of the present application can also be used as an additional viral inactivation method following a conventional/defatting disinfecting step.

After acid treatment, the bone tissue is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone tissue is immersed in solution to effect its defatting. Further, in accordance with this application, the demineralized bone tissue can be used immediately for preparation of the implant composition or it can be stored under aseptic conditions, advantageously in a critical point dried state prior to such preparation. In an embodiment, the bone tissue can retain some of its original mineral content such that the composition is rendered capable of being imaged utilizing radiographic techniques.

The bone tissue may be particulated. If the bone tissue is demineralized, the bone may be particulated before, during or after demineralization. As previously discussed, in some embodiments, the bone tissue may be monolithic and may not be particulated. Accordingly, while specific discussion is given to particulating bone, the methods disclosed herein and the nanoscale textured surfaces disclosed herein may be used with monolithic bones or implants, including, for example, surface demineralized implants or fully demineralized cortical bone implants.

The bone tissue may be milled and ground or otherwise processed into particles of an appropriate size before or after demineralization. The particles may be particulate or fibrous. The terms milling or grinding are not intended to be limited to production of particles of a specific type and may refer to production of particulate or fibrous particles. In certain embodiments, the particle size may be greater than 75 microns, such as ranging from about 100 to about 3000 microns, or from about 200 to about 2000 microns. After grinding, the bone particles may be sieved to select those particles of a desired size. In certain embodiments, the particles may be sieved though a 50 micron sieve, a 75 micron sieve, or a 100 micron sieve.

In yet a further embodiment, monolithic bone tissue is demineralized and particulated before drying. Accordingly, the bone tissue may be demineralized in monolithic pieces. The demineralized monolithic pieces may then be milled in a wet condition and critical point dried, for example using carbon dioxide as a medium.

In yet a further embodiment, monolithic bone is demineralized and dried before particulating (if done). Accordingly, the bone may be demineralized in monolithic pieces. The DBM is pressed in a wet condition and then critical point dried, for example using carbon dioxide as a medium. In alternatives of this embodiment, the demineralized and dried monolithic bone is not particulated and is processed as a monolithic implant.

Providing Demineralized Bone Matrix

In various embodiments, the process of this application can be used to decontaminate bone matrix compositions which comprise fibers. DBM includes the collagen matrix of the bone together with acid insoluble proteins including bone morphogenetic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM for use in the methods described in this application is prepared from elongated bone fibers which have been subjected to critical point drying. The elongated bone fibers employed in this application are generally characterized as having relatively high average length to average width ratios, also known as the aspect ratio. In various embodiments, the aspect ratio of the elongated bone fibers is at least from about 50:1 to about at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length be from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

To prepare the osteogenic DBM, a quantity of fibers is combined with a biocompatible carrier to provide a demineralized bone tissue.

Providing a Carrier

Generally, materials for the carrier may be biocompatible in vivo and optionally biodegradable. In some uses, the carrier acts as a temporary scaffold until replaced completely by new bone. Suitable carriers can be any number of compounds and/or polymers, such as polymer sugars, proteins, long chain hydrophilic block copolymers, reverse phase block copolymers, hyaluronic acid, polyuronic acid, mucopolysaccharide, proteoglycan, polyoxyethylene, surfactants, including the pluronics series of nonionic surfactants, and peptide thickener. Suggested classes of biocompatible fluid carrier would include polyhydroxy compound, polyhydroxy ester, fatty alcohol, fatty alcohol ester, fatty acid, fatty acid ester, liquid silicone, combinations thereof, and the like. Settable materials may be used, and they may set up either in situ, or prior to implantation. The bone fibers and carrier (or delivery or support system) together form an osteoimplant useful in clinical applications.

Examples of suitable biocompatible fluid carrier include, but are not limited to:

(i) Polyhydroxy compound, for example, such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

(ii) Polyhydroxy ester, for example, liquid and solid monoesters and diesters of glycerol can be used to good effect, the solid esters being dissolved up in a suitable vehicle, for example, propylene glycol, glycerol, polyethylene glycol of 200-1000 molecular weight. Liquid glycerol esters include monacetin and diacetin and solid glycerol esters include such fatty acid monoesters of glycerol as glycerol monolaurate, glyceryl monopalmitate, glyceryl monostearate. In various embodiments, the carrier herein comprises glyceryl monolaurate dissolved in glycerol or a 4:1 to 1:4 weight mixtures of glycerol and propylene glycol, poly (oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid.

(vi) Fatty acid ester, for example, polyoxyethylene-sorbitan-fatty acid esters, for example, mono- and tri-lauryl, palmityl, stearyl, and oleyl esters including of the type available under the trade name Tween from Imperial Chemical Industries; polyoxyethylene fatty acid esters including polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol, for example, of the type known and commercially available under the trade name IMWITOR®; sorbitan fatty acid esters, or of the type known and commercially available under the trade name Span, including sorbitan-monolauryl,-monopalmityl, -monostearyl, -tristearyl, -monooleyl and triolcylesters; monoglycerides, for example, glycerol monooleate, glycerol monopalmitate and glycerol monostearate, for example, as known and commercially available under the trade names Myvatex, Myvaplex and Myverol, and acetylated, for example, mono- and di-acetylated monoglycerides, for example, as known and commercially available under the trade name Myvacet; isobutyl tallowate, n-butylstearate, n-butyl oleate, and n-propyl oleate.

(vii) Liquid silicone, for example, polyalkyl siloxanes such as polymethyl siloxane and poly (dimethyl siloxane) and polyalkyl arylsiloxane.

In some embodiments of the implantable composition of this application, the liquid carrier is a liquid polyhydroxy compound, liquid polyhydroxy compound derivative, liquid solution of solid polyhydroxy compound, liquid solution of solid polyhydroxy compound derivative or combinations thereof. If necessary or desirable, in some embodiments, the liquid carrier can be dissolved or diluted with an appropriate solvent such that when combined with the demineralized bone fibers described herein a composition capable of being shaped or packed into a coherent mass which retains its shape and volume over the relatively long term, until the bone formation and remodeling process is completed, is provided. Thus, the polyhydroxy compound or polyhydroxy derivatives can be a liquid in the pure or highly concentrated state at ambient temperature, from about 15° C. to about 50° C., or it can be a solid or semi-solid at this temperature in which case it becomes necessary to dissolve the material in a solvent such as water, physiological saline, ethanol, glycerol, glucose, propylene glycol, polyethylene glycol of from 200-1000 molecular weight, or polyvinyl alcohol. In other embodiments, the liquid carrier can be made up of one or more liquid polyhydroxy compounds or derivatives in solution with one or more solid polyhdroxy compounds or derivatives.

The osteoinductive or biologically active composition may be configured to be moldable, extrudable, or substantially solid. The osteoinductive or biologically active composition may be configured to substantially retain its shape in water for a period of time. The osteoinductive or biologically active composition may form an osteoimplant useful in clinical applications. Suitable carriers may include surface demineralized bone; mineralized bone; nondemineralized cancellous scaffolds; demineralized cancellous scaffolds; cancellous chips; particulate, demineralized, guanidine extracted, species-specific (allogenic) bone; specially treated particulate, protein extracted, demineralized, xenogenic bone; collagen; synthetic hydroxyapatites; synthetic calcium phosphate materials; tricalcium phosphate, sintered hydroxyapatite, settable hydroxyapatite; polylactide polymers; polyglycolide polymers, polylactide-co-glycolide copolymers; tyrosine polycarbonate; calcium sulfate; collagen sheets; settable calcium phosphate; polymeric cements; settable poly vinyl alcohols, polyurethanes; resorbable polymers; and other large polymers; liquid settable polymers; and other biocompatible settable materials. The carrier may further comprise a polyol (including glycerol or other polyhydroxy compound), a polysaccharide (including starches), a hydrogel (including alginate, chitosan, dextran, pluronics, N,O-carboxymethylchitosan glucosamine (NOCC)), hydrolyzed cellulose, or a polymer (including polyethylene glycol). In embodiments wherein chitosan is used as a carrier, the chitosan may be dissolved using known methods including in water, in mildly acidic aqueous solutions, in acidic solutions.

The carrier may further comprise a hydrogel such as hyaluronic acid, dextran, pluronic block copolymers of polyethylene oxide and polypropylene, and others. Suitable polyhodroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Settable materials may be used, and they may set up either in situ, or prior to implantation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

Any suitable shape, size, and porosity of carrier may be used. In some embodiments, the carrier may be settable and/or injectable. Such carrier may be, for example, a polymeric cement, a suitable settable calcium phosphate, a settable poly vinyl alcohol, a polyurethane, or a liquid settable polymer. Hydrogel carriers may additionally impart improved spatial properties, such as handling and packing properties, to the osteoconductive composition. An injectable carrier may be desirable where the composition is used with a containment device. In addition, selected materials must be biocompatible in vivo and optionally biodegradable. In some uses, the carrier acts as a temporary scaffold until replaced by new bone. Polylactic acid (PLA), polyglycolic acid (PGA), and various combinations have different dissolution rates in vivo. In bone, the dissolution rates can vary according to whether the composition is placed in cortical or trabecular bone.

In certain embodiments, the carrier may comprise a shape-retaining solid made of loosely adhered particulate material with collagen. It may alternatively comprise a molded, porous solid, a monolithic solid, or an aggregate of close-packed particles held in place by surrounding tissue. Masticated muscle or other tissue may also be used. Large allogenic bone implants may act as a carrier, for example where their marrow cavities are cleaned and packed with DBM and, optionally, the osteoinductive factors.

In various embodiments, the carrier comprises an osteoinductive material such as a mineralized particulated material, osteoinductive growth factors, or partially demineralized bone. The mineralized particulated material may be TCP, hydroxyapatite, mineral recovered from bone, cancellous chips, cortical chips, surface demineralized bone, or other material. The osteoinductive material may be combined with a further carrier such as starch or glycerol. Accordingly, in some embodiments, the bone tissue may act as a carrier for the tissue-derived extract.

Where, in a particular implantable composition, the fibrous and/or non-fibrous elements exhibit a tendency to quickly or prematurely separate from the carrier component or to otherwise settle out from the composition such that application of a fairly homogeneous composition is rendered difficult or inconvenient, it can be advantageous to include within the composition an optional substance whose thixotropic characteristics prevent or reduce this tendency. Thus, for example, where the carrier component is glycerol and separation of fibrous and/or non-fibrous bone elements occurs to an excessive extent where a particular application is concerned, a thixotropic agent such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend the fibrous and/or non-fibrous elements, can be combined with the carrier in an amount sufficient to significantly improve the suspension-keeping characteristics of the composition.

Preparing a DBM Composition

To prepare a DBM composition according to one or more embodiments of this application, a quantity of demineralized bone fibers prepared as described above is combined with water or any other appropriate, biocompatible liquid to form a smooth, flowable, cohesive paste. The resultant implantable composition may be molded or injected into any desired shape and retains its shape, even when submersed in water, saline, or other aqueous solution. An additional benefit of the DBM fibers is that the resultant paste is injectable through an 18-gauge needle.

The liquid may be any biocompatible liquid, including water, saline solution, buffered solutions, serum, bone marrow aspirant, blood, platelet-rich plasma and the like and combinations thereof. Some biocompatible liquids suitable for use with the short DBM fibers, such as serum, bone marrow aspirant and blood, additionally contain osteoinductive factors that will promote bone growth at the site to which the composition is applied.

Providing Optional Additives

If desired, the fibrous and/or non-fibrous bone tissue of this application can be modified in one or more ways. In various embodiments, any of a variety of medically and/or surgically useful optional substances can be incorporated in, or associated with, the bone elements before, during, or after preparation of the implantable composition. Thus, in some embodiments, one or more of such substances can be introduced into the bone tissue, for example, by soaking or immersing the bone tissue in a solution or dispersion of the desired substance(s), by adding the substance(s) to the carrier component of the implantable composition or by adding the substance(s) directly to the implantable composition.

Medically/surgically useful substances which can be readily combined with the bone fibers, fluid carrier and/or implantable composition of this application include, for example, collagen, insoluble collagen derivatives, hydroxyapatite, and soluble solids and/or liquids dissolved therein, for example, antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, peptides, vitamins, inorganic elements, inorganic compounds, cofactors for protein synthesis, hormones; endocrine tissue or tissue fragments; synthesizers; enzymes such as collagenase, peptidases, oxidases; polymer cell scaffolds with paraenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenetic proteins (BMPs), transforming growth factor (TGF-beta), insulin-like growth factor (IGF-1) (IGF-2), platelet derived growth factor (PDGF), fibroblast growth factors (FGF), vascular endothelial growth factor (VEGF), angiogenic agents, bone promoters, cytokines, interleukins, genetic material, genes encoding bone promoting action, cells containing genes encoding bone promoting action; growth hormones such as somatotropin; bone digestors; antitumor agents; fibronectin; cellular attractants and attachment agents; immunosuppressants; permeation enhancers, for example, fatty acid esters such as laureate, myristate and stearate monesters of polyethylene glycol, surface active agents, enamine derivatives, α-keto aldehydes; nucleic acids; epidermal growth factor (EGF); all collagen types (not just type 1); non-collagenous proteins such as osteopontin, osteonectine, bone sialo proteins, vitronectin, thrombospondin, proteoglycans, decorin, biglycan, aggrecan, versican, tenascin, matrix gla protein hyaluronan; soluble and insoluble components of the immune system, soluble and insoluble receptors including truncated forms, soluble, insoluble and cell surface bound ligands including truncated forms; chemokines, bioactive compounds that are endocytosed; compounds capable of altering the membrane potential of cells, compounds capable of altering the monovalent and divalent cation/anion channels of cells; bone resorption inhibitors and stimulators; angiogenic and mitogenic factors; bioactive factors that inhibit and stimulate second messenger molecules; integrin adhesion molecules; clotting factors; externally expanded autograft or xenograft cells and any combinations thereof. The amounts of such optionally added substances can vary widely with optimum levels being readily determined in a specific case by routine experimentation.

The demineralized bone tissue produced with the bone fibers prepared by delipidation/terminal sterilization described herein may comprise a number of materials in combination, some or all of which may be in the form of fibers and/or particles. The matrix may comprise calcium phosphates. Driessens, et al. "Calcium phosphate bone cements," Wise, D. L., Ed., Encyclopedic Handbook of Biomaterials and Bioengineering, Part B, Applications New York: Marcel Decker; Elliott, Structure and Chemistry of the Apatites and Other Calcium Phosphates Elsevier, Amsterdam, 1994, each of which is incorporated by reference. Calcium phosphate matrices include, but are not limited to, dicalcium phosphate dihydrate, monetite, tricalcium phosphate, tetracalcium phosphate, hydroxyapatite, nanocrystalline hydroxyapatite, poorly crystalline hydroxyapatite, substituted hydroxyapatite, and calcium deficient hydroxyapatites. In some embodiments, the bone fibers may be added to a carrier.

In some embodiments, the demineralized bone may be further treated to affect properties of the bone. For example, the DBM may be treated to disrupt the collagen structure of the DBM. Such treatment may comprise collagenase treatment, heat treatment, mechanical treatment, or other. While demineralized bone is specifically discussed herein, in some embodiments, the teachings herein may be applied to non-demineralized bone, to partially demineralized bone, or to surface demineralized bone.

In accordance with various embodiments, the bone tissue provided herein may be used with growth factors, extracts, peptide hormones, or other additives to increase the osteoinductive capacity or that otherwise encourage cell or biological activity of the bone tissue or to impart other benefits to the bone tissue. It will be appreciated that the amount of additive used will vary depending upon the type of additive, the specific activity of the particular additive preparation employed, and the intended use of the composition. The desired amount is readily determinable by the user.

Any of a variety of medically and/or surgically useful optional substances can be incorporated in, or associated with, the osteoinductive factors either before, during, or after preparation of the osteoinductive or biologically active composition. Thus, for example, when demineralized bone fibers prepared by delipidation/terminal sterilization described herein are used to form the material, one or more of such substances may be introduced into the demineralized bone fibers, by soaking or immersing these bone fibers in a solution or dispersion of the desired substance(s).

In one embodiment, a tissue-derived extract may be added to the bone tissue. U.S. Pat. No. 8,357,384 discloses such extracts and addition of such extracts to DBM and is incorporated herein by reference. For example, a tissue-derived extract or partially demineralized bone may be added to the bone tissue. The extract may be derived from any suitable tissue, such as bone, bladder, kidney, brain, skin, or connective tissue. Further, the extract may be derived in any suitable manner. The extract may be allogeneic, autogeneic, xenogeneic, or transgenic. In embodiments wherein the extract is bone-derived, the bone may be cortical, cancellous, or corticocancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

Bone regeneration involves a multitude of cells, for example, cartilage, fibroblasts, endothelial cells besides osteoblasts. Accordingly, the bone tissue composition may be used to deliver stem cells, which offers the potential to give rise to different types of cells in the bone repair process. In one embodiment, the bone tissue composition further comprises a cell such as an osteogenic cell or a stem cell.

In various embodiments, the additive may comprise radiopaque substances, angiogenesis promoting materials, bioactive agents, osteoinducing agents, or other. Such materials would include without limitation barium sulfate, iodine-containing compounds, titanium and mineralized bone.

In certain embodiments, the additive is adsorbed to or otherwise associated with the bone tissue. The additive may be associated with the bone tissue through specific or non-specific interactions, or covalent or noncovalent interactions. Examples of specific interactions include those between a ligand and a receptor, an epitope or an antibody. Examples of nonspecific interactions include hydrophobic interactions, electrostatic interactions, magnetic interactions, dipole interactions, van der Waals interactions, or hydrogen bonding. In certain embodiments, the additive is attached to the bone tissue composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive or biologically active composition. An additive may be provided within the osteoinductive or biologically active composition in a sustained release format. For example, the additive may be encapsulated within biodegradable polymer nanospheres, or microspheres.

Flow additives according to this application can include, but are not limited to, small molecule organic compounds, polymeric/oligomeric materials, and solutions thereof. In some embodiments, when added to the implantable composition containing the bone fibers the viscosity thereof should be sufficiently changed to allow flow through a syringe needle of about 8-gauge or greater (greater number gauges of syringe needles have smaller diameters, thus requiring lower threshold viscosity through which they may flow), in some aspects, of about 12-gauge or greater, for example of about 14-gauge or greater, of about 15-gauge or greater, or of about 18-gauge or greater. Sufficient flow can be understood, in terms of syringe needles, to result in an injection force of not more than 50 pounds, and in some aspects, not more than 40 pounds. In another embodiment, the flow additive modifies the viscosity of the composition to which it is added such that the composition is capable of flowing through a syringe needle having a gauge size from about 8 to about 18, alternately from about 8 to about 15, from about 12 to about 18, or from about 12 to about 15.

When present, the amount of flow additive that can be added to the composition can be from about 0.01% to about 1.5% by weight of the fiber composition from about 0.1% to about 1% by weight, or from about 0.05% to about 1% by weight. In an alternate embodiment, the amount of flow additive can be from about 1.5% to about 5% by weight of the fiber composition. In an embodiment, the flow additive, when used, is present in an amount of about 0.5% by weight of the composition.

Suitable examples of flow additives can include, but are in no way limited to, hyaluronic acid; hyaluronate salts such as sodium, potassium, lithium, or the like, or a combination thereof; alginate salts such as sodium, potassium, lithium, or the like; starch compounds, which can be present in its natural form, in a destructured form, or in any number of chemically modified derivative forms (for example, alkyoxylated derivatives, esterified derivatives, ionically modified starches, oxidized starches, grafted starches, crosslinked starches, or the like, or combinations thereof); saturated, monounsaturated, and/or polyunsaturated oils, such as those extracted or isolated from plant and/or animal sources, including, but not limited to, sunflower, safflower, peanut, castor bean, sesame, coconut, soybean, corn, canola, olive, vegetable, palmitins, stearins, oleins, and the like, or derivatives or combinations thereof, as naturally extracted, as synthesized, or as modified or processed in some way, partially or fully hydrogenated, partially or fully dehydrogenated, partially or fully saponified, partially or fully acidified, partially halogenated, or the like; a wax including, but not limited to, hydrocarbon waxes (for example, polyolefin waxes, such as polyethylene wax, polypropylene wax, and the like, or copolymers thereof), oligoester waxes, monoester waxes, oligoether waxes, monoether waxes, and the like, or combinations thereof, as naturally extracted, as synthesized, or as modified or processed in some way, partially or fully hydrogenated, partially or fully dehydrogenated, partially or fully saponified, partially or fully acidified, partially halogenated, or the like; cellulosic compounds, including, but not limited to, native or synthetic cellulose, cotton, regenerated cellulose (for example, rayon, cellophane, or the like), cellulose acetate, cellulose propionate, cellulose butyrate, cellulose acetate-propionate, cellulose acetate-butyrate, cellulose propionate-butyrate, cellulose nitrate, methyl cellulose, ethyl cellulose, carboxymethyl cellulose, carboxyethyl cellulose, cellulose salts, and combinations or copolymers thereof, as naturally extracted, as synthesized, or as modified or processed in some way, including partially or fully esterified, partially or fully nitrated, partially or fully regenerated, partially or fully etherified, partially or fully acidified, partially or fully acid-neutralized, or the like, or combinations thereof; surface-active biomolecules or (co)polymers; poly(ethylene glycol) and/or poly(ethylene oxide) oligomers, homopolymers, or copolymers; autologous substances such as autologous bone marrow aspirates, autologous blood substances, or the like, or a combination thereof heterologous substances such as allogeneic bone marrow aspirates, xenogenic bone marrow aspirates, allogeneic blood substances, xenogenic blood substances, or the like, or a combination thereof or the like, or combinations thereof. In an embodiment, the flow additive comprises hyaluronic acid and/or a hyaluronate salt. In another embodiment, the flow additive comprises sodium hyaluronate. In an alternate embodiment, the flow additive can include chondroitin, glucosamine, hyaluronic acid, a salt thereof, or a mixture thereof.

In one or more embodiments, an additive is included in the DBM composition to further modify the handling characteristics of the composition, such as viscosity and moldability. The additive may be a biocompatible polymer, such as a water-soluble cellulosic, or a natural polymer, such as gelatin. The additive may be added to either the dry DBM component or the liquid component. The additive may be used to at least partially coat the DBM fibers prior to combining them with the liquid carrier. Non-limiting examples of additives suitable for use in the DBM composition include gelatin, carboxymethyl cellulose, hydroxypropyl methylcellulose, methylcellulose, hydroxyethyl cellulose, other cellulose derivatives, alginate, hyaluronic acid, sodium salts, polyvinyl pyrrolidones, polyvinyl alcohol, arabic gum, guar gum, xantham gum, chitosans, and poloxamers.

As previously indicated, the implantable composition of this disclosure can be freshly prepared just by mixing desired quantities of the demineralized fibrous bone elements, fluid carrier and optional component(s), if any, in any suitable sequence of separate mixing, adsorption, rehydration or drying operations or all at once. Thus, the demineralized fibrous bone elements prepared by delipidation/terminal sterilization described herein can be mixed with the optional ingredients(s) and thereafter combined with the fluid carrier component, the demineralized fibrous bone elements can be mixed with the fluid carrier followed by addition of the optional ingredient(s) or the optional ingredients can be added to the fluid carrier followed by addition of the demineralized fibrous bone elements. Variations of these and other sequences of mixing are, of course, possible. In various embodiments, the implantable composition can include non-fibrous bone elements. In other embodiments, the fibrous elements and fluid carrier are mixed substantially simultaneously such that the fibrous elements of the implantable composition are entangled and the non-fibrous bone elements are thoroughly mixed in the entangled fibrous bone elements.

The amount of demineralized bone fibers prepared by delipidation/terminal sterilization described herein which can be incorporated into the implantable composition can vary widely with amounts of about 99% weight, about 95% by weight, about 90% by weight, about 85% by weight 70% by weight. In various embodiments, the amount of the non-fibrous bone elements which can be incorporated into the implantable composition can vary widely with amounts from about 10 to about 90 weight percent, and in some aspects, from about 20 to about 70 weight percent. The ratio of fibrous to non-fibrous bone elements can vary between about 0.2:1 to about 1:0.2. The balance of the composition being made up of fluid carrier and optional ingredient(s), if any.

The bone tissue composition may be completely insoluble or may be slowly solubilized after implantation. Following implantation, the composition may resorb or degrade, remaining substantially intact for at least one to seven days or for two or four weeks or longer and often longer than 60 days. The composition may thus be resorbed prior to one week, two weeks, three weeks, or other, permitting the entry of bone healing cells.

Covering Material for Contaminated Bone Tissue

In some embodiments, the covering utilized to contain the contaminated bone tissue for further treatment may be used for retaining of particulate or morselized bone tissues (the substance provided in the covering), optionally to provide a focus or concentration of biological activity. In some embodiments, the covering may be used for maintaining materials (the substance provided in the covering) in spatial proximity to one another, possibly to provide a synergistic effect. In some embodiments, the delivery system may be used to control availability of substances provided within the delivery system to cells and tissues of a surgical site over time. In some embodiments, the covering may be used for delivery through a limited opening, such as in minimally invasive surgery or mini-open access. In some embodiments, the covering may be used to deliver morselized or particulated materials (the substance provided in the covering) in pre-measured amounts.

In various embodiments, the covering can contain a demineralized allograft material. The covering limits, and in some embodiments eliminates bone tissue migration and maintains bone tissue density. The covering containing demineralized allograft material, may be configured to conform to surrounding bony contours or implant space. In some embodiments, the delivery system provides a pathway for healing/cell penetration and tissue ingrowth. Thus, the covering may facilitate transfer of a substance out of the covering or transfer or surrounding materials at the surgical site, such as cells and tissues, into the covering.

The covering useful to contain the contaminated bone tissue may have a single compartment or may have a plurality of compartments. Thus, in one embodiment, the covering is dual-compartment and comprises first and second compartments. A first substance may be provided in the first compartment and a second substance may be provided in the second compartment. The second compartment may be adjacent to, apart from, inside, or surrounding the first compartment. Materials forming the first compartment and the second compartment may be the same or different. Selection of materials, positioning of the compartments, and other factors relating to the first and second compartments may be chosen to achieve simultaneous or sequential delivery or release of a substance or substances.

The covering may comprise a structural material and, in some embodiments, a functional material. The structural material may comprise a mesh material, a polymeric material, or other. The functional material may comprise, for example, a radiopaque material, a bactericidal material, or other material.

In various embodiments, in accordance with the specific application for which the covering is being used, the covering may be rigid, may be flexible, may be non-elastic, or may be elastic. The covering material may be braided, woven, non-woven shape memory, particulate, threaded, porous, or non-porous.

The covering may participate in, control, or otherwise adjust the release of the substance. For example, the covering may act as a selectively permeable membrane and/or may be porous, with the level of porosity being related to the nature of the substances inside the covering. Thus, the material for and configuration of the covering may be selected or adjusted based on desired release characteristics. Specific properties that may be adjusted include thickness, permeability, porosity, strength, flexibility, elasticity, and others of the covering material. It is to be appreciated that some of these properties may depend on others. For example, the thickness and porosity of the material may contribute to its strength, flexibility, and elasticity.

In some embodiments, the covering may be porous to fluid and/or cells, may be biocompatible, and may be resistant to rupture (including should the substance provided therein swell). In some embodiments, the covering with the demineralized allograft material provided therein may be loadbearing. The covering may be resorbable or non-resorbable. The covering may provide increased handling properties, may have irrigation resistance, and/or may support cellular penetration. Flexibility of the covering may be selected to suit particular applications. In some applications, it may be desirable to have a flexible covering.

If the covering is made from a resorbable material, the covering degrades and disappears after a period of time. If the covering is not made of a resorbable material, the covering remains in the body. Tissue ingrowth may occur to bind the host tissue to the substance provided within the covering. Tissue ingrowth through and around the covering, between the host tissue and the substance provided within the covering, may be promoted via openings in the covering.

In various embodiments, the covering may comprise a porous material or a mesh material. The size of the pores of the covering may be designed to permit cellular infiltration (approximately several microns to several millimeters), but may also be designed specifically to exclude cells for the inside of the covering (e.g. approximately 0.45 microns) and only allow diffusion of small molecules (proteins and hormones). Thus, the covering may act to control access to the interior of the delivery system by cells. In embodiments comprising more than one compartment, characteristics of the covering material may be varied between compartments. Generally, the porosity, flexibility, strength, or any other characteristic of one compartment may vary from that characteristic of the other compartment.

The covering may be formed of a resorbable or non-resorbable, natural or synthetic biocompatible material. In some embodiments, more than one material may be used, including as multiple layers. For example, in an embodiment comprising two compartments, one or more materials may be used for the first compartment and a different material or materials may be used for the second compartment. For example, one compartment or portions thereof may be made of material or materials that provide a desired property or properties relative to other compartments or portions thereof, such as increased or decreased resorbability or stiffness, or the different compartments or portions thereof may be imparted with different drug delivery properties, etc. Alternatively, all compartments may comprise the same material or mixtures of materials. Where the characteristics of the material are varied between compartments or over the surface of a single compartment, the pores of the first compartment or portion thereof may be larger than the pores of the second compartment.

The covering may comprise any suitable structure for delivering a substance in vivo. Thus, as described, the covering may comprise a mesh. In other embodiments, the covering may comprise a polymeric structure with a chamber provided therein. The chamber may be filled with a substance for delivering in vivo, such as demineralized allograft material, fully mineralized bone tissue, or others disclosed herein.

In some embodiments, the covering may expand when placed in the body. Expansion can be provided in at least two ways: the covering may be compressed such that the covering expands when placed in the body or the covering may be made of a material that expands when it comes in contact with water or other bodily fluids, either by way of liquid absorption or by stretching when the materials inside it absorb liquid and themselves expand. In some embodiments, the covering may comprise a shape memory material such as copper-zinc-aluminum-nickel alloy, copper-aluminum-nickel alloy, and nickel-titanium (NiTi) alloy. Reinforcing materials such as cortical bone, calcium phosphates, etc. may be incorporated into the structure of the covering to reinforce it.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers. The coating may be selected such that it has a resorption time wherein it is resorbed by the body and the material within the covering is permitted to exit through openings in the covering.

Exemplary Covering Materials

A covering according to an aspect of the present disclosure may comprise demineralized allograft material and at least one of bioerodible polymers, bioabsorbable polymers, biodegradable biopolymers, synthetic polymers, copolymers and copolymer blends and combinations thereof. Exemplary materials may include biopolymers and synthetic polymers such as human skin, human hair, bone sheets, collagen, fat, thin crosslinked sheets containing fibers and/or fibers and chips, degradable sheets made from polyethylene glycol (PEG), chitosan sheets, alginate sheets, cellulose sheets, hyaluronic acid sheet, as well as copolymer blends of poly (lactide-co-glycolide) PLGA.

Exemplary materials may include polymeric material, woven material and braided material, non-woven; shape memory material; using outer particles to contain inner particles; attach particles to threads; add porosity to mesh fibers; non-porous materials; non-porous materials. In some embodiments, materials may be used for portions of the covering, such as for a compartment of the covering that is substantially impenetrable.

In some embodiments, the covering may comprise a mesh material. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly (lactic acid) (PLA), poly (glycolic acid) (PGA), poly (lactic acid-glycolic acid) (PLGA), polydioxanone, PVA, polyurethanes, polycarbonates, and others. Other suitable materials include carbon fiber, metal fiber, and various meshes. In other embodiments, the covering may comprise non-woven material such as a spun cocoon or shape memory materials having a coil shape or shape memory alloys.

Generally, the covering may be formed of any natural or synthetic structure (tissue, protein, carbohydrate) that can be used to form a covering configuration. Thus, the covering may be formed of a polymer (such as polyalkylenes (e.g., polyethylenes, polypropylenes, etc.), polyamides, polyesters, poly(glaxanone), poly(orthoesters), poly(pyrolicacid), poly(phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other. Various collagen materials can be used, alone or in combination with other materials, including collagen sutures and threads. Any suitable collagen material may be used, including known collagen materials. Some examples include polymer or collagen threads woven, or knitted into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds; etc.

In some embodiments, mesh fibers may be treated to impart porosity to the demineralized allograft material that is in fiber form. This may be done, for example, to PLA, PLGA, PGA, and other fibers. One suitable method for treating the mesh fibers comprises supercritical carbon dioxide, supercritical nitrogen, or supercritical water treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles, demineralized allograft material, or the like. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

In yet other embodiments, the covering may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a non-porous covering.

In particular, in various embodiments, the device may comprise a bioerodible, a bioabsorbable, and/or a biodegradable biopolymer that may provide immediate release, or sustained release of the clonidine. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG and/or PEG may be used as a plasticizer for PLGA, but other polymers/excipients may be used to achieve the same effect. mPEG imparts malleability to the resulting formulations. In some embodiments, these biopolymers may also be coated on a medical device to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the medical device ranges from about 5 microns to about 250 microns or 5 microns to about 200 microns to delay release from the medical device.

Functional Material Characteristics

The covering material may have functional characteristics. Alternatively, other materials having functional characteristics may be incorporated into the covering in addition to bone tissue. Functional characteristics may include radiopacity, bacteriocidity, source for released materials, tackiness, or the like. Such characteristics may be imparted substantially throughout the covering or at only certain positions or portions of the covering.

Suitable radiopaque materials include, for example, ceramics, mineralized bone, ceramics/calcium phosphates/calcium sulfates, metal particles, fibers, and iodinated polymer. Polymeric materials may be used to form the covering and be made radiopaque by iodinating them. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the covering or may be provided substantially throughout the covering. Thus, for example, in a tubular covering, a radiopaque marker may be provided at a tip of the tubular covering. Such marker may facilitate placement of the covering. Radiopaque materials may be incorporated into the covering and/or into the substance for delivery by the covering. Further, radiopaque materials may be provided at only some locations on the covering such that visualization of those locations provides indication of the orientation of the covering in vivo.

The covering itself may be designed to release materials during degradation of the covering material. Thus, bone morphogenetic proteins (BMPs), growth factors, antibiotics, angiogenesis promoting materials (discussed more fully below), bioactive agents (discussed more fully below), or other actively releasing materials may be incorporated into the covering material such that as the covering material is degraded in the body, the actively releasing material is released. For example, an actively releasing material may be incorporated into a biodegradable polymer covering such as one manufactured of a biodegradable polyester such as poly(lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers). In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXOR® products available from Osteotech™) may be used in the covering.

In some embodiments, the covering may comprise a material that becomes tacky upon wetting. Such material may be, for example, a protein or gelatin based material. Tissue adhesives, including mussel adhesive proteins and cyanoacrylates, may be used to impart tackiness to the covering. In further examples, alginate or chitosan material may be used to impart tackiness to the covering. In further embodiments, an adhesive substance or material may be placed on a portion of the covering or in a particular region of the covering to anchor that portion or region of the covering in place at an implant site.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of decontaminating bone tissue, the method comprising: contacting the bone tissue having contaminants therein with carbon dioxide to decontaminate the bone tissue and form carbon dioxide having contaminants; collecting the carbon dioxide having contaminants; separating the contaminants from the collected carbon dioxide; and removing the contaminated carbon dioxide, purifying the contaminated carbon dioxide with supercritical fluid, liquefying the purified carbon dioxide and using liquid purified carbon dioxide as a cooling fluid.

2. A method of decontaminating bone tissue of claim 1, comprising treating the contaminated bone tissue with ethanol gradient dehydration.

3. A method of decontaminating bone tissue of claim 2, further comprising flushing with liquid carbon dioxide the contaminated bone tissue treated with ethanol gradient dehydration.

4. A method of decontaminating bone tissue of claim 3, further comprising subjecting the contaminated bone tissue to critical point dehydration and/or supercritical carbon dioxide treatment; and releasing the carbon dioxide at a controlled rate.

5. A method of decontaminating bone tissue of claim 4, wherein the temperature and pressure of carbon dioxide is raised to or above 31.1° C. and 1100 psi.

6. A method of decontaminating bone tissue of claim 4, wherein supercritical carbon dioxide treatment is carried out at approximately 105° C. and approximately 7000 psi.

7. A method of decontaminating bone tissue of claim 1, wherein contaminated carbon dioxide is separated by bubbling through water and/or an organic solvent to remove contaminants comprising lipids, disease causing pathogens, viruses or bacteria.

8. A method of decontaminating bone tissue of claim 7, further comprising treating the carbon dioxide bubbled through water and/or the organic solvent with acid treatment, filtering and liquefying the carbon dioxide.

9. A method of decontaminating bone tissue of claim 8, wherein the liquefied carbon dioxide is purified to 99.9% free of lipids, disease causing pathogens, viruses or bacteria.

10. A method of decontaminating bone tissue of claim 8, further comprising generating processing charts including vanishing interfacial tension and carbon dioxide pressure.

11. A method of decontaminating bone tissue of claim 1, wherein the bone tissue comprises bone fibers, bone chips, bone particles, bone matrices or mixtures thereof.

12. A method of decontaminating bone tissue of claim 1, further comprising providing a delivery vehicle for the bone tissue having contaminants, the delivery vehicle comprising a carrier or covering.

13. A method of decontaminating bone tissue of claim 1, wherein the method of decontaminating the bone tissue is a multiple batch process.

* * * * *